US004001723B2

United States Statutory Invention Registration [19]

[11] Reg. Number: H1723

[45] Published: Apr. 7, 1998

Leuenberger et al.

[54] PROCESS FOR PRODUCING GASOLINE BLENDING COMPONENTS FROM JET RANGE AND HEAVIER AROMATICS

[76] Inventors: Ernest L. Leuenberger, 14241 Olive Tree Cir., Tustin, Calif. 92680; John C. Burger, 7319 Marina Pacifica Dr., Key 11, Long Beach, Calif. 90803

[21] Appl. No.: 584,809

[22] Filed: Jan. 11, 1996

Related U.S. Application Data

[63] Continuation of Ser. No. 146,275, Oct. 28, 1993, abandoned, which is a continuation of Ser. No. 943,962, Sep. 11, 1992, abandoned.

[51] Int. Cl.[6] ..... C07C 5/00

[52] U.S. Cl. ..... 585/310

[58] Field of Search ..... 585/301, 302, 585/304, 319, 323, 475; 208/78, 79

[56] References Cited

U.S. PATENT DOCUMENTS

| | | | |
|---|---|---|---|
| 2,996,447 | 8/1961 | Porter et al. | 208/66 |
| 3,692,858 | 9/1972 | Brewer et al. | 260/672 |
| 3,716,596 | 2/1973 | Bowes | 260/671 |
| 3,719,586 | 3/1973 | Benner | 208/66 |
| 3,763,260 | 10/1973 | Pollitzer | 260/672 |
| 3,855,328 | 12/1974 | Hedge | 260/668 |
| 3,873,439 | 3/1975 | Pollitzer | 208/66 |
| 3,928,174 | 12/1975 | Bonacci et al. | 208/80 |
| 3,948,758 | 4/1976 | Bonacci et al. | 208/92 |
| 3,957,621 | 5/1976 | Bonacci et al. | 208/60 |
| 3,996,305 | 12/1976 | Osborne | 260/672 |
| 4,112,056 | 9/1978 | Chen et al. | 423/329 |
| 4,136,128 | 1/1979 | Haag et al. | 260/671 |
| 4,140,622 | 2/1979 | Herout et al. | 208/93 |
| 4,157,950 | 6/1979 | Frilette et al. | 208/135 |
| 4,172,813 | 10/1979 | Feinstein et al. | 585/475 |
| 4,237,329 | 12/1980 | Kamiyama et al. | 585/474 |
| 4,320,242 | 3/1982 | Onodera et al. | 585/489 |
| 4,393,262 | 7/1983 | Kaeding | 585/467 |
| 4,454,364 | 6/1984 | Farcasiu et al. | 585/470 |
| 4,469,908 | 9/1984 | Burress | 585/467 |
| 4,504,690 | 3/1985 | Forbus et al. | 585/466 |
| 4,554,394 | 11/1985 | Forbus et al. | 585/474 |
| 4,577,049 | 3/1986 | Rudnick | 585/486 |
| 4,827,069 | 5/1989 | Kushnerick et al. | 585/415 |
| 5,053,573 | 10/1991 | Jorgensen | 585/467 |
| 5,082,983 | 1/1992 | Breckenridge et al. | 208/113 |
| 5,177,280 | 1/1993 | Juguin et al. | 585/323 |
| 5,177,285 | 1/1993 | Van Opdorp et al. | 585/323 |

*Primary Examiner*—Charles T. Jordan
*Assistant Examiner*—Meena Chelliah

[57] ABSTRACT

A process for producing gasoline blending components from a heavy hydrocarbon composition comprising alkyl aromatics by transalkylation of said alkyl aromatics with benzene is provided. In a preferred embodiment, the process comprises (a) feeding said heavy hydrocarbon composition comprising alkyl aromatics and said benzene as feed to a cracking unit; and (b) contacting said alkyl aromatics and said benzene with cracking catalyst at catalytic cracking conditions of elevated temperature and pressure to produce transalklyation products. Also, provided is a process, for producing gasoline blending components from the jet aromatics content of jet fuel and reducing the benzene content of a benzene-rich light gasoline stream, said process comprising operating a catalytic cracker at conventional catalytic cracking conditions and reacting in said catalytic cracking reactor said aromatic jet fuel with said benzene-rich light gasoline stream to convert at least a portion of said benzene-rich gasoline and at least a portion of said jet aromatics to toluene and xylenes. The catalytic cracker can be a fluid catalytic cracker, moving bed catalytic cracker and fixed bed catalytic cracker.

27 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR PRODUCING GASOLINE BLENDING COMPONENTS FROM JET RANGE AND HEAVIER AROMATICS

This application is a continuation of application Ser. No. 08/146,275, filed on Oct. 28, 1993, now abandoned, which is a continuation of application Ser. No. 07/943,962, filed on Sep. 11, 1992, now abandoned.

BACKGROUND OF THE INVENTION

1. Field of the Invention

In one aspect, this invention relates to transalkylation of aromatics. In another aspect, this invention relates to conversion of aromatics of a heavy hydrocarbon composition comprising alkyl aromatics by transalkylation of the alkyl aromatics with benzene. In still another aspect, this invention relates to a process for producing gasoline blending components from jet range aromatics and simultaneously reducing the benzene content of light gasoline. In a still further aspect, this invention relates to the conversion of components of jet fuel and benzene-rich light gasoline to toluene, xylenes and other desirable gasoline blending components.

2. Description of the Related Art

Until recently, benzene has been a blending component that refiners have desired in light gasoline because benzene improves octane; however, in view of the Clear Air Act of 1990, many jurisdictions are now limiting the amount of benzene that can be contained in gasoline due to benzene's contribution to automobile engine exhaust toxins. Hydrotreating light gasoline to remove benzene or extracting the benzene for use as a chemical feedstock are two of the options most frequently proposed from the prior art to solve benzene-related refining issues. Hydrotreating, however, substantially reduces the octane of light gasoline and also requires an expensive expansion of hydrotreating facilities, including the costs associated with additional hydrogen production facilities. Concentration of benzene for use as a chemical feedstock requires expensive solvent purification facilities and also reduces gasoline octane and exposes the refiner to the business risk of contributing to an oversupply of benzene. Extracted benzene can be reacted with light olefins to make alkyl benzene for octane enhancement to improve the octane supply problem but additional capital is required. Light olefin availability is also a problem, since most refineries have hydrofluoric or sulfuric acid alkylation units, and those units are preferably fed all of the available light olefins produced in the refinery in order to make high octane, aromatic free alkylate.

In addition to benzene-related issues, the alkyl aromatics in light jet fuel, in the boiling range of about 300° F. to about 430° F. were formerly valuable as high octane gasoline blending components. Many jurisdictions are now limiting the final boiling point of gasoline to temperatures in the range of about 300° F., which eliminates this profitable use for such high aromatics light jet fuel and may contribute to an octane shortage. Disposing of the heavy jet aromatics boiling between 430° and 525° F. has also become more difficult due to the limits certain jurisdictions have placed on diesel aromatic content. In these jurisdictions, converting these aromatics to naphthenes in a hydrotreater or cracking them to gasoline in a hydrocracker have become substantially the only economically viable upgrading routes in the present state of refining art; however, expanded hydrotreating or hydrocracking requires substantial capital investment compared to the blending operations that have been eliminated by the applicable jurisdictions' mandates as to fuel compositions. There is thus a need for a refining option that will reduce the amount of aromatic jet that must be hydrotreated and will reduce the required hydrotreating investment.

Fluid catalytic cracking of hydrocarbons is typically a method of choice that refiners employ to convert heavy hydrocarbon feedstocks into lighter products. Principal catalytic cracking products are high octane gasoline and oldfin feed for alkylation units; however, a jet range fuel is produced by fluid catalytic cracking and such jet fuel is typically high in aromatics and is generally known to be particularly difficult to hydrotreat. A fluid unit also produces benzene by cracking alkylbenzenes. These characteristics of a fluid unit tend to worsen the jet aromatics and gasoline benzene problems. For example, U.S. Pat. No. 5,082,983 relates to the reaction of light reformate containing benzene with heavy feedstock in a fluid unit to convert at least a portion of the benzene to gasoline aromatics; however, such operation provides only a limited conversion of benzene because the heavy feed to the catalytic cracker produces toluene and xylenes that shift the equilibrium towards higher yields of benzene and heavy alkyl aromatics.

There is thus the need for a process which maximizes the conversion to high octane gasoline components of unwanted refinery blend components such as benzene and heavy alkyl aromatics. There is also a need for a process which removes benzene and heavy alkyl aromatics from blend streams, with minimal capital investment.

SUMMARY OF THE INVENTION

We have discovered that the transalkylation reaction between benzene and alkyl benzenes can be promoted to equilibrium in a cracking unit operated in accordance with this invention. This has the surprising result of consuming both benzene and jet aromatics when such are contacted with cracking catalyst, preferably in the absence of toluene, xylenes and other gasoline aromatics. We have found that the conversion of heavy aromatics is highest when there are substantially no other alkyl aromatics are in the feed to the cracking unit.

Accordingly, it is an object ,of the present invention to provide a process to convert heavy jet range aromatics to desirable gasoline range materials and simultaneously reduce the benzene content of light gasoline. It is another object of this invention to provide a process for adding jet fuel and light gasoline to a conventional catalytic cracker operating at conventional catalytic cracking conditions but in the absence of the conventional heavy feed to convert at least a portion of the benzene and at least a portion of the jet aromatics to toluene, xylenes and other desirable gasoline aromatics.

The present invention thus solves issues facing a refiner whose gasoline blend streams contain excessive benzene and heavy alkyl aromatics. Preferred embodiments of this invention thus adapt one mature process, catalytic cracking, in a novel way, to solve problems caused by lack of process flexibility with and excess equipment and process costs associated with hydrotreating, another mature process.

In one embodiment of this invention, a process for producing gasoline blending components from aromatics of a heavy hydrocarbon composition comprising alkyl aromatics, by transalkylation of the alkyl aromatics with benzene comprises (a) feeding the heavy hydrocarbon composition comprising alkyl aromatics and the benzene as feed to a cracking unit; and, (b) contacting the alkyl aromatics and the benzene with cracking catalyst at catalytic cracking conditions, preferably at elevated temperature and pressure, to produce transalklyation products. The transalkylation products so produced are preferred high octane aromatic gasoline blending components, and we have found that such transalkylation proceeds at cracking conditions in the presence of cracking catalyst. The term "heavy hydrocarbon composition", as used in the Specification and claims, means a hydrocarbon composition having a boiling range determined by American Society of Testing and Materials (ASTM) distillation procedure D86 of about 300° F. (initial boiling point) to about 690° F. (end point), which range includes jet range and heavier aromatic compounds. In preferred variations of this embodiment, the heavy hydrocarbon composition is a jet range composition which boils in the range of about 300° F. to about 525° F. The term "gasoline", as used in the Specifications and Claims, means a mixture of liquid hydrocarbons having an initial boiling point somewhere in the range of of about 65° F. to about 140° F. and a final boiling point in the range of about 250° F. to about 450° F., and the term "gasoline blending components" means hydrocarbons boiling with the gasoline boiling range, with preferred embodiments of this invention producing gasoline blending components having an end point in the range of about 285° F. to about 350° F. The term "transalkylation", as used in the Specification and Claims, means the transfer of a hydrocarbon group or radical from one hydrocarbon compound to another, as for example, the formation of two moles of toluene by transalkylation of benzene with a xylene, and transalkylation may include removal of a hydrocarbon group or radical from one aromatic hydrocarbon and substitution of such removed group or radical for a hydrogen atom in another aromatic compound, as for example, the conversion of benzene to toluene by the addition of a methyl group which is removed from a xylene. In one variation of this embodiment, the cracking unit produces conventionally produced alkyl aromatic products, including but not limited to toluene, m-xylene, o-xylene, p-xylene, ethylbenzene, and the like, and the benzene and the jet range and heavier alkyl aromatics from the heavy hydrocarbon composition are fed to the cracking unit in a manner wherein the transalkylation products do not contact the cracking catalyst in the presence of the conventionally produced alkyl aromatic products. Preferably, the benzene is a component of a concentrated benzene stream comprising in the range of about 5 volume percent to about 100 volume percent benzene, and more preferably, the alkyl aromatics are a component of a concentrated alkyl aromatic stream comprising in the range of about 20 volume percent to about 100 volume percent alkyl aromatics. It is also preferred that the feed to the cracking unit contains less than about 5 volume percent total of toluene, xylenes, and ethylbenzene. In another variation of this embodiment, the combined benzene feed and the alkyl aromatics feed comprise more than about eighty percent of the total feed to the cracking unit, and such may occur wherein there is substantially no or very little heavy hydrocarbon feed to the cracking unit. It is preferred that the benzene and the alkyl aromatics be fed to the cracking unit at separate feed locations, although such separate feeding is not required.

In a preferred variation of this embodiment of this invention, the cracking unit is a fluid catalytic cracking unit which comprises a first riser, a stripping zone, and a catalyst regenerator which produces regenerated catalyst. The cracking unit may also comprise a column for recovery and separation of products of the cracking reaction. Such cracking unit is preferably operated at conventional fluid catalytic cracking conditions, using a hot acidic cracking catalyst, all as well known in the art. Preferably, the benzene and the alkyl aromatics are fed, for transalkylation, to the fluid catalytic cracking unit at separate feed locations. For example, it is preferred that the benzene be fed to the first riser at a feed location before the alkyl aromatics are fed to the first riser wherein the benzene is first to contact catalyst. In a preferred variation, the fluid catalytic cracking unit comprises a second riser and the benzene and composition comprising alkyl aromatics are fed to the first riser and conventional cracking feed is fed to the second riser. In one variation, the benzene and the composition comprising alkyl aromatics are the sole feed to the first riser and the second riser is operated conventionally. In this manner, the transalkylation products in the first riser do not contact, in a riser reactor and the presence of hot reactive catalyst, the products of the conventional feed in the second riser.

In another variation of this embodiment of this invention, the benzene and the alkyl aromatics are fed to the stripping zone of the fluid catalytic cracking unit and are contacted with regenerated catalyst. It is preferred that the benzene and alkyl aromatics be contacted with the regenerated catalyst before being fed to the stripping zone, as this can allow the benzene to be contacted with the regenerated catalyst before the alkyl aromatics are contacted with the regenerated catalyst; however, the regenerated catalyst can be fed separately to the stripping zone and fluidized therein with the catalyst which is present already in the stripping zone. Thus, in one variation, the stripping zone comprises a fluidized bed of spent catalyst to which regenerated catalyst and the benzene and the composition comprising alkyl aromatics are fed.

Those skilled in the art understand that preferred embodiments of this invention have been discussed with reference to a cracking unit which is a fluid catalytic cracking, and the invention is not limited thereto. In other embodiments of this invention, the cracking unit is a moving bed catalytic cracking unit. In still other embodiments of this invention the cracking unit is a fixed bed cracking unit. A fluidized bed of catalyst is not required for the transalkylation reactions to occur, and for reasons of process and apparatus economics a fixed catalyst bed transalkylation reactor may be used in conjunction with a fluid catalytic cracking unit to share a common product recovery column. Thus, in one variation, the cracking unit comprises a cracking riser for cracking conventional heavy feed to cracked products and fixed bed cracking reactor for contacting the benzene and the alkyl aromatics with cracking catalyst.

In another embodiment of this invention, a process, for producing gasoline blending components from the jet aromatics content of jet fuel and reducing the benzene content of a benzene-rich light gasoline stream, comprises operating a catalytic cracker at conventional catalytic cracking conditions and reacting in the catalytic cracking reactor the aromatic jet fuel with the benzene-rich light gasoline stream to convert at least a portion of the benzene-rich gasoline and at least a portion of the jet aromatics to toluene and xylenes. Preferably, the light gasoline comprises a high benzene concentration and contains less than 5 volume percent of other aromatics. In a preferred variation of this embodiment, the catalytic cracker comprises two reactor risers and the reaction between benzene and jet aromatics occurs in one of the two reactor risers while cracking of a conventional heavy feed to lighter products occurs in one of the two reactor risers. Preferably the jet aromatics are at least one component of the lighter products cracked from the conventional heavy feed.

In another embodiment of this invention, a process for producing gasoline blending components from the jet aromatics content of jet fuel and reducing the benzene content of a light gasoline comprises operating a fluidized bed reactor with conventional fluidized catalytic cracking catalyst at conventional catalytic cracking conditions and reacting in the fluidized bed reactor the aromatic jet fuel with the light gasoline to convert at least a portion of the benzene and at least a portion of the jet aromatics to toluene and xylenes. Preferably, the fluidized bed reactor is the stripping zone of a fluid catalytic cracker which also cracks conventional heavy feed to lighter products. In one variation, the jet aromatics are a component of the lighter products cracked from the conventional heavy feed. In a preferred variation, the light gasoline contains no toluene, xylenes, ethylbenzene or other alkyl aromatic compounds.

In a still further embodiment of this invention, a process, for producing gasoline blending components from the jet aromatics content of jet fuel and reducing the benzene content of a light gasoline, the process comprising operating a moving bed reactor with conventional moving bed catalytic cracking catalyst at conventional catalytic cracking conditions and reacting in the moving bed reactor the jet aromatics with the light gasoline to convert at least a portion of the benzene and at least a portion of the jet aromatics to toluene and xylenes.

In another embodiment of this invention, a process, for producing gasoline blending components from the jet aromatics content of jet fuel and reducing the benzene content of a light gasoline comprising, the process comprises operating a fixed bed reactor with an acidic cracking catalyst at hydrocracking conditions and reacting in the fixed bed reactor the jet aromatics with the light gasoline to convert at least a portion of the benzene and at least a portion of the jet aromatics to toluene and xylenes. Preferred hydrocracking conditions include elevated temperature in the range of about 800° F. to about 1150° F. and elevated pressure in the range of about 500 psia to about 2000 psia, and the presence of free hydrogen, all of such conditions being well known in the art, and adjustable to met transalkylation conditions preferred by each refiner in the practice of this invention.

The practice of preferred embodiments of this invention allows transalkylation to effectively proceed in a existing catalytic cracking unit, with minimum costs for modifications, while avoiding the limits that would be placed on conversion if equilibrium were established between the cracked products conventionally produced in the cracking unit and the products of the transalkylation reaction.

DESCRIPTION OF PREFERRED EMBODIMENTS

This invention is further illustrated with reference to the drawings wherein, for purpose of illustration of preferred embodiments, it being understood that this invention is not limited thereto.

Figure 1:
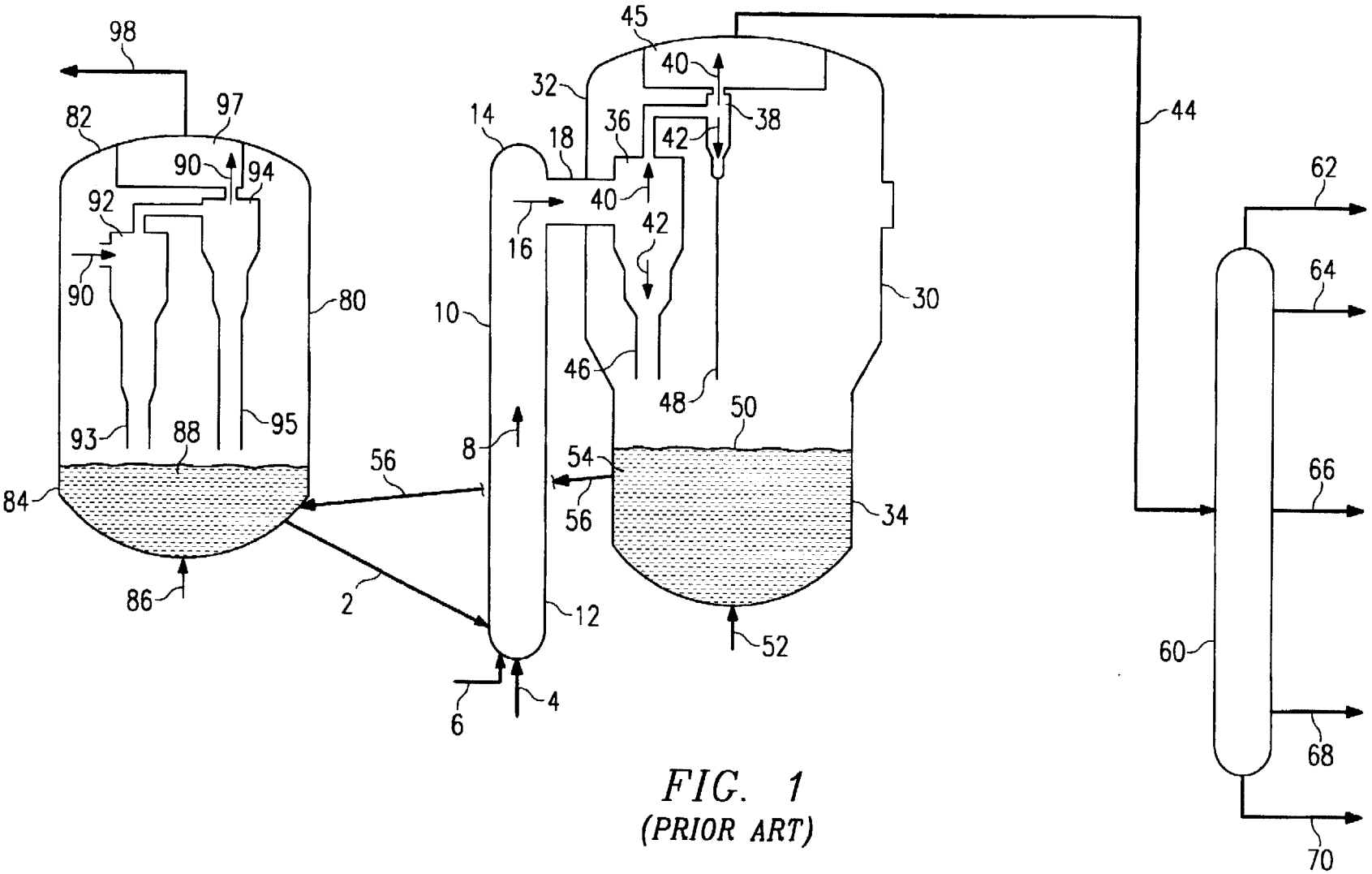
FIG. 1 (PRIOR ART)
FIG. 1 is schematic representation of a prior art riser cracking fluid catalytic cracking unit, having a conventional heavy hydrocarbon feed to the riser.

FIG. 1 is a schematic representation of a prior art riser cracking fluid catalytic cracking unit, the principle components of which are a riser 10, a reaction vessel 30, a main column 60 and regenerator 80. The riser 10 has a lower end 12 and a discharge zone 14. Hot acidic regenerated catalyst in conduit 2 is directed from the regenerator 80 and is charged to the lower end 12 of the riser 10. Such catalysts 2 are well known in the art. Heavy hydrocarbonaeous feed 4 is also charged to the lower end 12 of the riser 10 where atomizing steam 6 is also added. A reactive mixture 8 of catalyst 2 and heavy feed 4 rises as a dilute phase upward thought the riser 10 to the discharge zone 14 of the riser 10. The conventional feed 4 cracks in riser 10 to produce cracked reaction products which include gasoline alkyl aromatics. The temperature in the discharge zone 14 of the riser 10 is preferably maintained in the range of about 480° C. to about 615° C. (about 900° F. to about 1150° F.) and, more preferably in the range of about 480° C. to about 538° C. (about 900° F. to about 1000° F.) and preferably at a pressure in the range of about 30 psia to about 40 psia. The riser top temperature is preferably adjusted by adjusting the feed ratio to the riser 10 of hot regenerated catalyst 2 to heavy hydrocarbon feed 4, although the feed 4 to the riser 4 may be preheated and the preheat temperature conditions may be increased or decreased. Riser 10 effluent mixture 16 of coked catalyst and reaction products are directed via conduit 18 to the reactor 30. The reactor 30 has a catalyst/product separation zone 32 and a stripping zone 34. In the catalyst/product separation zone 32, riser 10 effluent mixture 16 is directed to cyclones 36 and 38 where reaction products 40 are separated from spent catalyst 42 and reaction products 40 are discharged into reactor 30 discharge zone 45. Reaction products 40 are fed from discharge zone 45 via conduit 44 to main column 60 and are separated into fractions such as gasoline and lighter vapors 62, heavy naphtha 64, light cycle oil 66, heavy cycle oil 68, and main column 60 bottoms 70. Spent catalyst 42 is directed from cyclones 36 and 38 via diplegs 46 and 48 to the reactor 30 stripping zone 34 where bed level 50 of catalyst is stripped via stripping steam 52 to recover absorbed or entrained hydrocarbons from the catalyst 50 to form a fluidized bed of stripped catalyst 54. Stripped catalyst 54 is fed via conduit 56 to regenerator 80 which has a catalyst/flue gas separation zone 82 and a spent catalyst combustion zone 84. Combustion air 86 is charged to the spent catalyst combustion zone 84 to form a fluidized catalyst bed 88 in regenerator 80 where coke deposits are removed from the spent catalyst 56 via combustion and hot regenerated catalyst 2 and combustion flue gas 90 are formed. Combustion flue gas 90 is directed to cyclones 92 and 94 where entrained catalyst fines are separated out and are directed via diplegs 93 and 95 to catalyst bed 88, as flue gas 90 is discharged from discharge zone 97 out of regenerator 80 via conduit 98.

Figure 2:
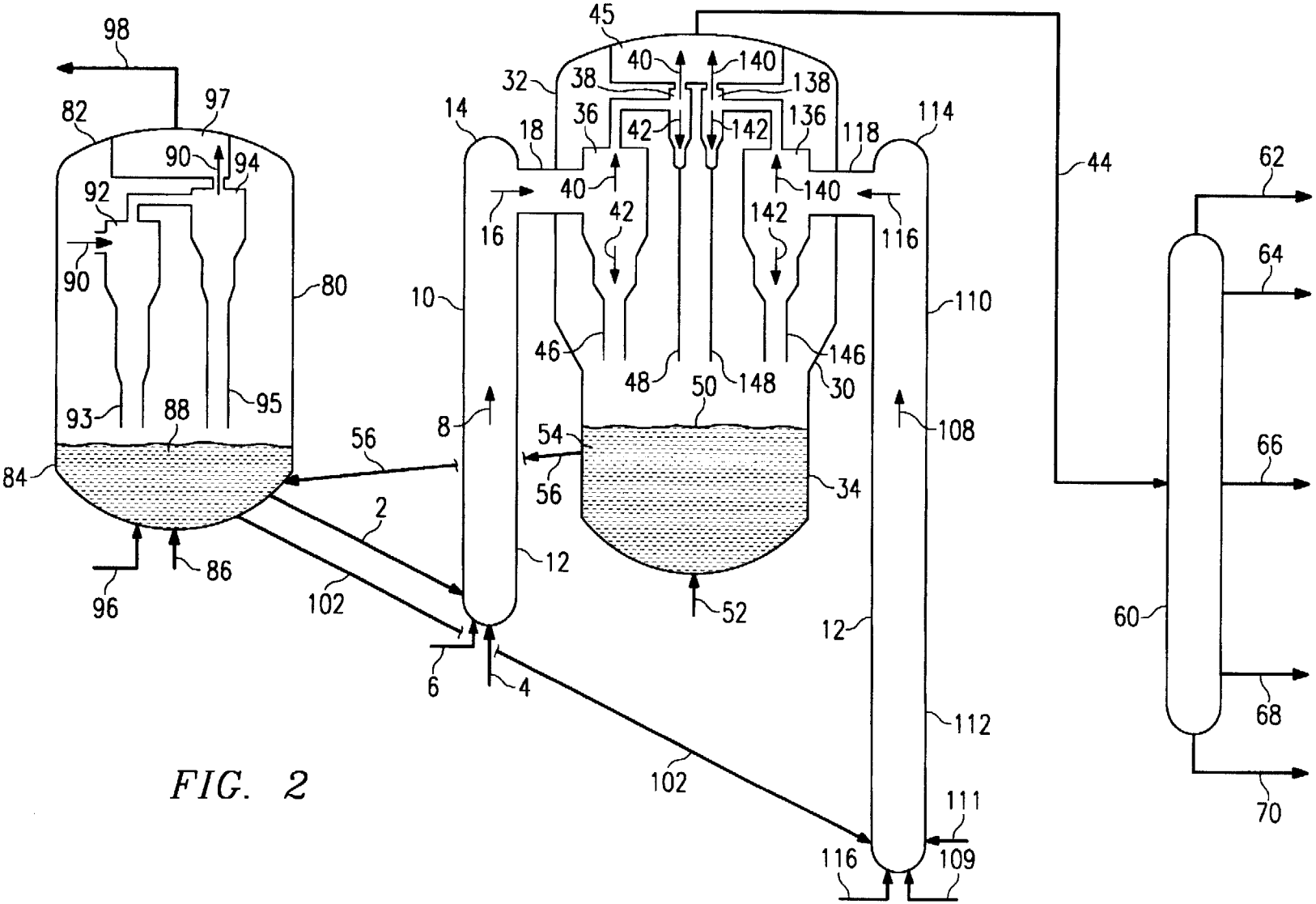
FIG. 2 is schematic representation of one embodiment of this invention wherein a concentrated benzene stream and a composition comprising alkyl aromatics are fed to and reacted within a transalkylation riser of a fluid catalytic cracking unit adapted to have a cracking riser and a transalkylation riser and conventional heavy hydrocarbon feed is fed to and cracked within the cracking riser.

FIG. 2 is an embodiment of this invention, being a combination of a cracking process with a transalkylation process. In the discussion of FIG. 2, the same numbers as used in FIG. 1 will be used in FIG. 2 to refer to the same or similar items. FIG. 2 illustrates one preferred embodiment of this invention wherein a riser fluid catalytic cracking unit is adapted, by the addition of a transalkylation riser which converts heavy aromatics and benzene into high octane gasoline. The process unit is configured to have a second riser 110, which riser has a lower end 112 and a discharge zone 114. Concentrated benzene is charged to riser 110 via conduit 109, and a composition comprising a concentrated amount of alkyl aromatics such as light gasoline is charged to riser 110 via conduit 111. Hot regenerated catalyst in conduit 102 is directed from the regenerator 80 and is charged to the lower end 112 of the riser 110. Preferably, no heavy hydrocarbonaeous feed 4 is charged to 110, which is reserved for transalkylation of the alkyl aromatics 111 with benzene 109. Atomizing steam 116 may also be added. A reactive mixture 108 of catalyst 102 and alkyl aromatics 111 and benzene 109 rises as a dilute phase upward thought the riser 110 to the discharge zone 114 of the riser 110. The benzene 109 reacts with the alkyl aromatics 111 to form toluene, xylenes, and other gasoline alkyl aromatics. Riser 110 effluent mixture 116 of coked catalyst and transalkylation reaction products comprising high octane gasoline are directed via conduit 118 to the reactor 30. In the catalyst/product separation zone 32 of the reactor 30, riser 110 effluent mixture 116 is directed to cyclones 136 and 138 where transalkylation products 140 are separated from spent catalyst 142.

Transalkylation products 140 produced in riser 110 and reaction products 40 produced in riser 10 are mixed in the reactor discharge zone 45, and at this point, the catalyst 2 and 102 has been removed by cyclones 36, 38, 136, and 138, and since hot catalyst is not present, the alkyl aromatics produced by cracking conventional feed 4 in riser 10 cannot shift the transalkylation equilibrium to convert the toluene, xylenes and other alkyl aromatics produced in riser 110 back to benzene and heavy alkyl aromatics.

The mixed stream of reaction products 40 and transalkylation products 140 is fed via conduit 44, along with cracking reaction products 40, to main column 60, where the combined products streams 40 and 140 are separated into fractions such as gasoline and lighter vapors 62, heavy naphtha 64, light cycle oil 66, heavy cycle oil 68, and main column 60 bottoms 70. In one variation of this embodiment, at least a portion of the heavy naphtha 64 is fed via conduit 164 as a portion of the alkyl aromatics feed 111 to the riser 110. Spent catalyst 142 is directed from cyclones 136 and 138 via diplegs 146 and 148' to the reactor 30 stripping zone 34 where bed level 50 of catalyst is stripped via stripping steam 52 to recover absorbed or entrained hydrocarbons. Although combustion in the regenerator 80 of coke on spent catalyst 56 provides the fuel to heat balance conventional cracking units, coke made from the transalkylation reactions in riser 110 may be insufficient for heat balance in the practice of variations of this embodiment of this inventions. Supplemental fuel 96, such as a torch oil, is preferably fed to the regenerator 80 as required, for heat balance. In preferred variations, a torch oil 96 is added to the regenerator 80 to adjust temperature in discharge zones 14 and 114 of the risers 10 and 110, respectively.

In preferred variations of this embodiment, riser 10 and riser 110 are each operated at selected conditions based upon operational data for each such riser to produce a desired product yield.

Thus, in the embodiment of this invention shown in FIG. 2, the cracking riser 10 and transalkylation riser 110 only require one reactor 30, one main column 60 and one regenerator 80. A relatively low cost, preferred transalkylation apparatus can thus be constructed by adapting an existing fluid cracking unit with the addition of a second riser 110 for transalkylation, a catalyst feed means 102 to second riser 110 and catalyst/product separation cyclones 136 and 138 in reactor 30.

Figure 3:
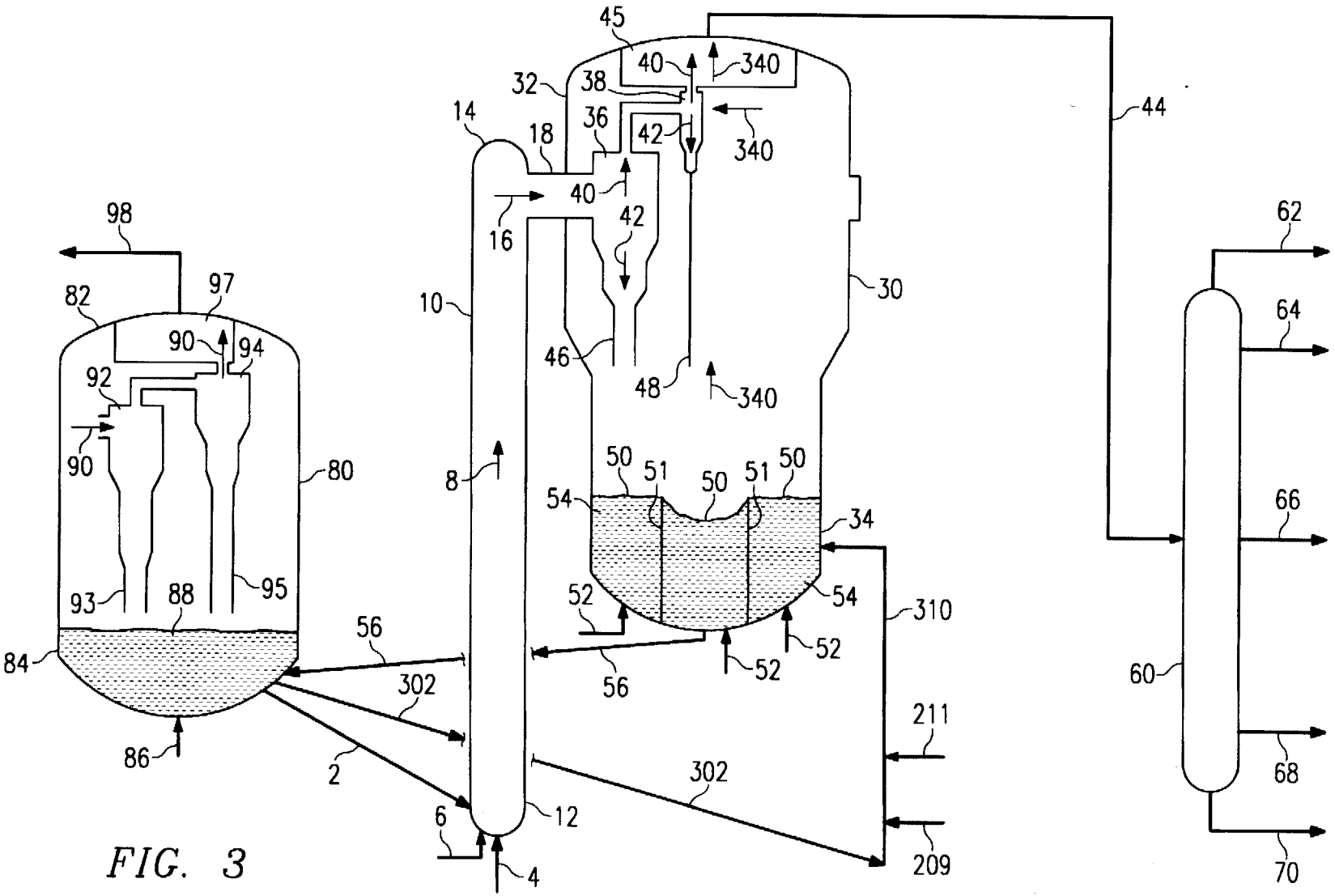
FIG. 3 is schematic representation of another embodiment of this invention wherein a light gasoline and a jet fuel are injected for transalkylation into the fluidized bed of the stripping zone of the reactor of a fluid catalytic cracking unit.

FIG. 3 illustrates another preferred embodiment of this invention, being a combination of a cracking process with a transalkylation process. In the discussion of FIG. 3, the same numbers as used in FIGS. 1 and 2 will be used in FIG. 3 to refer to the same or similar items. In the embodiment illustrated in FIG. 3, a benzene-rich light gasoline 209 and a jet fuel comprising alkyl aromatics 211 are contacted with hot regenerated catalyst 302 in conduit 310 and are fed for transalkylation into the fluidized bed 54 of the stripping zone 34 of the reactor 30 of a fluid catalytic cracking unit having multiple fluidizing steam input ports 52 and having catalyst support members 51, preferably in a cylindrical shape, and more preferably placed near the center of the stripping zone 52 to create an annulus around and into which catalyst 54 flows from the outer portion of the stripping zone 34 over the support members 51 and further flows into conduit 56. The reactor 30 passes the transalkylation products 340 upward through vent (not shown) in cyclone 38 to discharge zone 45, where such transalkylation products 340 are mixed with reaction products 40 and are passed to the main column 60 via conduit 44 for recovery of high octane alkyl aromatics.

EXAMPLE 1

A laboratory scale fluid catalytic cracking unit, comprising a riser, regenerator, and a stripper catalyst bed, was fed, in a continuous manner, a composition containing 12.1 volume percent C6 to C8 material and 87.9 volume percent C9+ material. Benzene was 10.5 weight percent of the feed. The feed contained no toluene, or C2–C5 material. Commercial fluid catalytic cracking catalyst was employed, and a weight/weight ratio of catalyst to feed of 26/1 was maintained. The reactor riser temperature was operated at 1070° F., and the pressure measured at the base of the riser was near atmospheric pressure, being at about 25 inches of water. A nominal amount of steam was added to the base of the riser for atomization. The operation resulted in a calculated space velocity, in the reaction zone, of 6 weight hourly space velocity (WHSV), which is the ratio products perhour to weight of catalyst in the reaction zone. The reactor product was sampled. The following are the sample test results:

| Yields, | wt % | Yields, | vol % |
|---|---|---|---|
| C2– | 5.6 | C3's | 14.2 |
| Benzene | 8.8 | C4's | 11.6 |
| Toluene | 9.7 | C5's | 6.3 |
| C8's | 17.7 | C6 to C8 | 39.1 |
| Coke | 8.2 | C9+ | 33.0 |

EXAMPLE 2

The same feed composition, containing 12.1 volume percent C6 to C8 material and 87.9 volume percent C9+ material, was fed in a continuous manner to the same laboratory cracking unit employed in Example 1, except that in this Example 2, the feed composition was not fed to the riser but was fed, instead, to the stripper catalyst bed. No other feed was fed to the bed containing hot regenerated catalyst. Since the same feed was employed to the bed, benzene remained 10.5 weight percent of the feed, and the feed contained no toluene, or C2–C5 material. The same commercial fluid catalytic cracking catalyst was employed, and a weight/weight ratio of catalyst to feed of 32/1 was maintained. The reactor riser temperature was operated at 930° F. A nominal amount of steam was added to the base of the riser for catalyst conveyance. The operation resulted in a calculated space velocity, in the bed reaction zone, of 0.2 WHSV. The reactor product was sampled. The following are the sample test results:

| Yields, | wt % | Yields, | vol % |
|---|---|---|---|
| C2– | 1.5 | C3's | 13.8 |
| Benzene | 2.4 | C4's | 22.6 |
| Toluene | 1.9 | C5's | 10.4 |
| C8's | 6.1 | C6 to C8 | 11.6 |
| Coke | 5.7 | C9+ | 42.2 |

In comparing the results of Examples 1 and 2, the lower space velocity of the bed reaction of Example 2 was found to be more effective at transalklyation of benzene converting about 75% of the benzene as compared to about 25% in Example 1. Also, the products of the bed reaction of Example 2 were mainly of a more desirable class suitable for feed to an existing refinery alkylation unit, while the riser reaction products of Example 1 included more gas and aromatic gasoline.

While the invention has been described in conjunction with presently preferred embodiments, it is obviously not limited thereto. For example, referring to FIG. 2, a concentrated benzene stream and a composition comprising alkyl aromatics may be fed to a riser 10 of cracking unit which also has fed to such riser 10 conventional heavy feed 4, all within the scope of the claims of this invention.

What is claimed is:

1. A process for producing gasoline blending components from a hydrocarbon composition comprising jet range alkyl aromatics and which boils in a range of from about 300° F. to about 690° F. by transalkylation of said jet range alkyl aromatics with benzene, said process comprising:

a. feeding said hydrocarbon composition comprising said jet range alkyl aromatics and said benzene as feed to a second reaction zone of a cracking unit, said cracking unit separately cracking in a first reaction zone and in the presence of cracking catalyst, a heavy feed comprising hydrocarbons which boil at a temperature greater than about 690° F. to a cracked product which comprises a first alkyl aromatic product;

b. contacting said hydrocarbon composition comprising said jet range alkyl aromatics and said benzene with a cracking catalyst at catalytic cracking conditions in the second reaction zone to produce transalkylation products, said contact conducted such that the transalkylation products do not contact the cracking catalyst in the presence of said first alkyl aromatic product produced by cracking said heavy feed in the first reaction zone;

c. separating the cracking catalyst from the cracked product of the first reaction zone;

d. separating the cracking catalyst from the transalkylation products of the second reaction zone; and e. thereafter mixing the cracked product of the first reaction zone and the transalkylation products of the second reaction zone.

2. A process in accordance with claim 1 wherein said transalkylation products are aromatic-containing gasoline blending components.

3. A process in accordance with claim 1 wherein said benzene is a component of a concentrated benzene stream comprising in the range of about 5 volume percent to about 100 volume percent benzene.

4. A process in accordance with claim 1 wherein said jet range alkyl aromatics are a component of a concentrated alkyl aromatic stream comprising in the range of about 20 volume percent to about 100 volume percent of said jet range alkyl aromatics.

5. A process in accordance with claim 1 wherein said hydrocarbon composition feed to said cracking unit contains less than about 5 volume percent total of toluene, xylenes, and ethylbenzene.

6. A process in accordance with claim 1 wherein said benzene and said jet range alkyl aromatics comprise more than about eighty percent of the total feed to the cracking unit.

7. A process in accordance with claim 1 wherein said benzene and said jet range alkyl aromatics are fed to said cracking unit at separate feed locations.

8. A process in accordance with claim 1 wherein said cracking unit is a fluid catalytic cracking unit which comprises a first riser, a stripping zone, and a catalyst regenerator which produces regenerated catalyst.

9. A process in accordance with claim 8 wherein said benzene and said jet range alkyl aromatics are fed to said fluid catalytic cracking unit at separate feed locations.

10. A process in accordance with claim 9 wherein said benzene is fed to said first riser at a feed location before said jet range alkyl aromatics are fed to said first riser wherein said benzene is first to contact catalyst.

11. A process in accordance with claim 8 wherein said fluid catalytic cracking unit comprises a second riser and said benzene and said hydrocarbon composition comprising said jet range alkyl aromatics are fed to said first riser and said heavy feed is fed to said second riser.

12. A process in accordance with claim 11 wherein said benzene and said composition comprising said jet range alkyl aromatics are the sole feed to said first riser.

13. A process in accordance with claim 8 wherein said benzene and said jet range alkyl aromatics are fed to said stripping zone of said fluid catalytic cracking unit and are contacted with regenerated catalyst.

14. A process in accordance with claim 13 wherein said benzene is contacted with said regenerated catalyst before said jet range alkyl aromatics are contacted with said regenerated catalyst.

15. A process in accordance with claim 13 wherein said stripping zone comprises a fluidized bed of spent catalyst to which regenerated catalyst and said benzene and said composition comprising said jet range alkyl aromatics are fed.

16. A process in accordance with claim 1 wherein said cracking unit is a moving bed catalytic cracking unit.

17. A process in accordance with claim 1 wherein said cracking unit is a fixed bed cracking unit.

18. A process in accordance with claim 1 wherein said cracking unit comprises a cracking riser for cracking said heavy feed to cracked products and a fixed bed cracking reactor for contacting said benezene and said hydrocarbon composition comprising said jet range alkyl aromatics with said cracking catalyst.

19. A process, for producing gasoline blending components from the jet aromatics content of a jet fuel comprising hydrocarbons which boil in a range of from about 300° F. to about 525° F. and reducing the benzene content of a benzene-rich light gasoline stream, said process comprising: operating a catalytic cracker unit at catalytic cracking conditions wherein said catalytic cracker cracks a heavy feed comprising hydrocarbons which boil at a temperature greater than about 690° F. in a first reaction zone and in the presence of cracking catalyst to a lighter product which comprises a first alkyl aromatic product; reacting separately in a second reaction zone of said catalytic cracking unit said aromatic jet fuel with said benzene-rich light gasoline stream by contact with a cracking catalyst to convert at least a portion of said benzene-rich gasoline and at least a portion of said jet aromatics to an aromatic-containing product comprising toluene and xylenes, said contact conducted such that the toluene and xylenes do not contact the cracking catalyst in the presence of said first alkyl aromatic product produced by cracking said heavy feed in the first reaction zone; separating out the cracking catalyst from the lighter product and the aromatic-containing product; and thereafter mixing the lighter product and the aromatic-containing product.

20. A process in accordance with claim 19 wherein said light gasoline comprises benzene in a concentration of from about 5 volume percent up to about 100 volume percent and less than about 5 volume percent of other aromatics.

21. A process in accordance with claim 19 wherein said catalytic cracker comprises a first reactor riser and a second reactor riser and said reaction between benzene and jet aromatics occurs in said first reactor riser while cracking of said heavy feed to lighter products occurs in said second reactor riser.

22. A process in accordance with claim 21 wherein said jet aromatics are a component of said lighter products cracked from said heavy feed.

23. A process for producing gasoline blending components from the jet aromatics content of a jet fuel comprising hydrocarbons which boil in a range of from bout 300° F. to about 525° F. and reducing the benzene content of a light gasoline stream, the process comprising: operating a fluidized bed reactor unit with a conventional fluidized catalytic cracking catalyst at catalytic cracking conditions wherein said reactor cracks in a first reaction zone a heavy feed comprising hydrocarbons which boil at a temperature greater than about 690° F. to a lighter product which comprises a first alkyl aromatic product; and, reacting separately in a second reaction zone of said fluidized bed reactor unit said aromatic jet fuel with said light gasoline by contact with the cracking catalyst to convert at least a portion of said benzene and at least a portion of said jet aromatics to an aromatic-containing product comprising toluene and xylenes, said contact conducted such that the toluene and xylenes do not contact the cracking catalyst in the presence of said first alkyl aromatic product produced by cracking said heavy feed in the first reaction zone; separating out the cracking catalyst from the lighter product and the aromatic-containing product; and, thereafter mixing the lighter product and the aromatic-containing product.

24. A process in accordance with claim 23 wherein said fluidized bed reactor is the stripping zone of a fluid catalytic cracker.

25. A process in accordance with claim 24 wherein said jet aromatics are a component of said lighter products cracked from said heavy feed.

26. A process for producing gasoline blending components from the jet aromatics content of a jet fuel comprising hydrocarbons which boil in a range of from about 300° F. to about 525° F. and reducing the benzene content of a light gasoline stream, said process comprising: operating a moving bed reactor unit with a moving bed catalytic cracking catalyst at catalytic cracking conditions wherein said reactor unit in a first reaction zone cracks a heavy feed comprising hydrocarbons which boil at a temperature greater than about 690° F. to a lighter product which comprises a first alkyl aromatic product; and, reacting separately in a second reaction zone in said moving bed reactor said jet aromatics with said light gasoline by contact with the cracking catalyst to convert at least a portion of said benzene and at least a portion of the jet aromatics to an aromatic-containing product comprising toluene and xylenes, said contact conducted such that the toluene and xylenes do not contact the cracking catalyst in the presence of said first alkyl aromatic product produced by cracking said heavy feed in the first reaction zone; separating out the cracking catalyst from the lighter product and the aromatic-containing product; and, thereafter mixing the lighter product and the aromatic-containing product.

27. A process for producing gasoline blending components from the jet aromatics content of a jet fuel comprising hydrocarbons which boil in a range of from about 300° F. to about 525° F. and reducing the benzene content of a light gasoline stream, said process comprising operating a fixed bed reactor unit with an acidic cracking catalyst at hydrocracking conditions wherein a first reaction zone of said reactor unit cracks a heavy feed comprising hydrocarbons which boil at a temperature greater than about 690° F. to a lighter product which comprises a first alkyl aromatic product; and, reacting separately in a second reaction zone of said fixed bed reactor said jet aromatics with said light gasoline by contact with the cracking catalyst to convert at least a portion of said benzene and at least a portion of said jet aromatics to an aromatic-containing product comprising toluene and xylenes, said contact conducted such that the toluene and xylenes do not contact the cracking catalyst in the presence of said first alkyl aromatic product produced by cracking said heavy feed in the first reaction zone; separating out the cracking catalyst from the lighter product and the aromatic-containing product; and thereafter mixing the lighter product and the aromatic-containing product.

* * * * *